United States Patent [19]

Swift

[11] Patent Number: 5,329,061
[45] Date of Patent: Jul. 12, 1994

[54] CRYSTALLIZATION PROCESS FOR PARA-XYLENE RECOVERY USING TWO-STAGE RECOVERY SECTION

[75] Inventor: John D. Swift, Hindhead, England

[73] Assignee: UOP, Des Plaines, Ill.

[21] Appl. No.: 69,320

[22] Filed: Jun. 1, 1993

[51] Int. Cl.$^5$ .............................. C07C 7/00; C07C 7/14
[52] U.S. Cl. ..................................... 585/805; 585/814; 585/815
[58] Field of Search ........................ 585/805, 814, 815

[56] References Cited

U.S. PATENT DOCUMENTS

| | | | |
|---|---|---|---|
| 2,724,007 | 11/1955 | Tegge | 260/674 |
| 2,823,241 | 2/1958 | Bennett et al. | 260/674 |
| 2,866,833 | 12/1958 | Spiller, Jr. | 260/674 |
| 2,913,503 | 11/1959 | Bozich et al. | 260/666 |
| 3,049,575 | 8/1962 | Schaeffer | 260/674 |
| 3,177,265 | 4/1965 | Lammers | 260/674 |
| 3,197,525 | 7/1965 | Schaeffer | 260/674 |
| 3,825,614 | 7/1974 | Bemis et al. | 585/814 |
| 3,959,978 | 6/1976 | Lindley et al. | 585/814 |
| 4,025,573 | 5/1977 | Hathway | 585/814 |

*Primary Examiner*—Asok Pal
*Assistant Examiner*—Nhat Phan
*Attorney, Agent, or Firm*—Thomas K. McBride; John F. Spears, Jr.; Reginald K. Taylor

[57] ABSTRACT

In a combination crystallization/xylene isomerization process for producing para-xylene crystals, the recovery section is modified to accommodate crystallizing and separating para-xylene crystals at two different temperatures (a higher temperature followed by a lower temperature). The benefit is a reduction in the overall energy cost of the process.

17 Claims, 1 Drawing Sheet

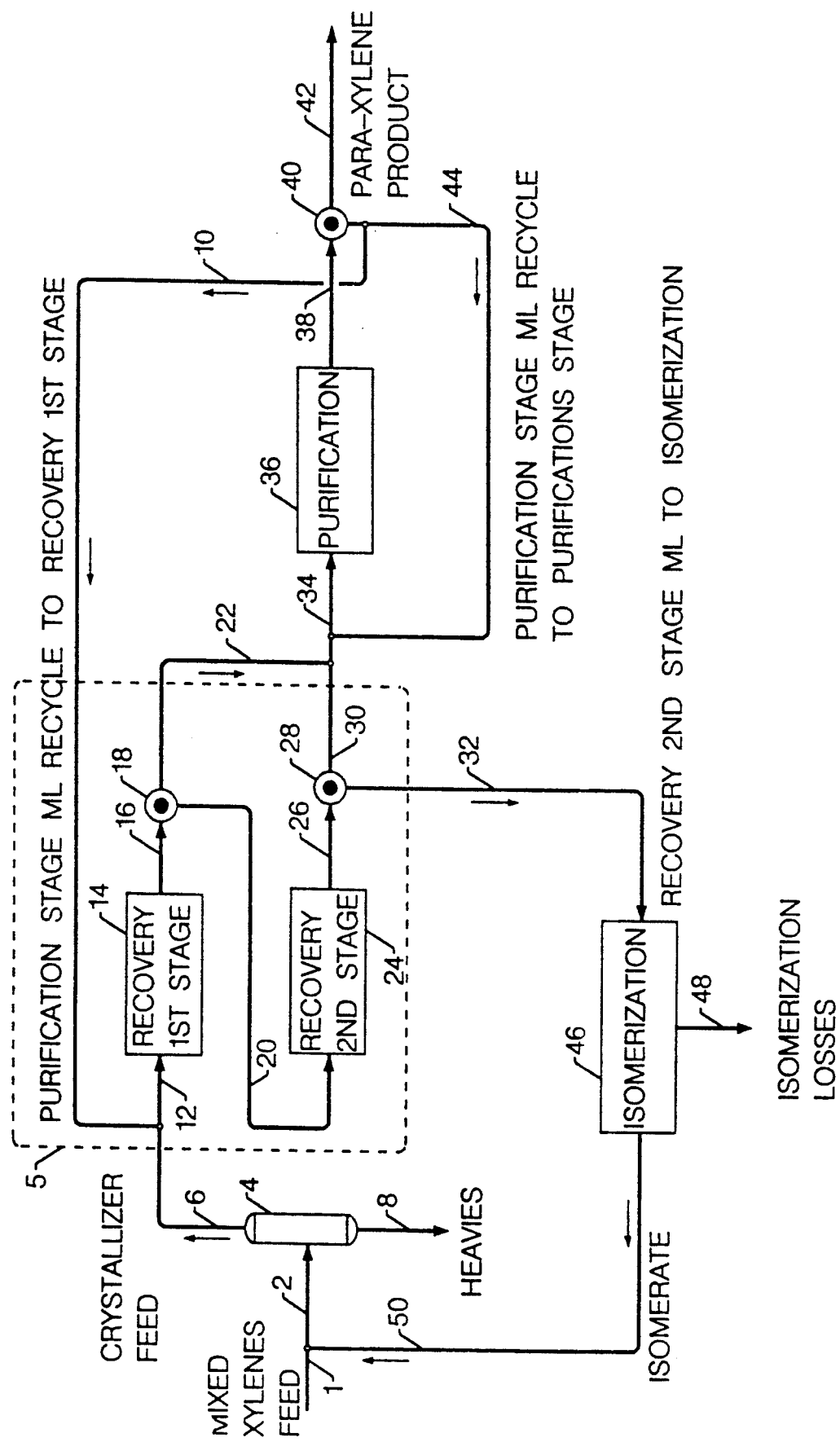

CRYSTALLIZATION PROCESS FOR PARA-XYLENE RECOVERY USING TWO-STAGE RECOVERY SECTION

Field of the Invention

The present invention relates to an improved process for the production of para-xylene. More specifically, the present invention involves the production of high purity para-xylene crystals from a mixture of xylene isomers using a process which crystallizes and separates para-xylene at two temperatures (the first being higher than the second) to reduce energy consumption.

BACKGROUND OF THE INVENTION

Xylene isomers consist of para-xylene, meta-xylene, ortho-xylene and ethylbenzene. Para-xylene is used in the manufacture of terephthalic acid which in turn is subsequently employed in the manufacture of various synthetic fibers, such as polyester. Meta-xylene is used for the manufacture of insecticides, isophthalic acid or alkyd resins. Ortho-xylene can be used as material for plasticizers.

Xylenes are found in substantial quantities in coke oven light oils and certain virgin and reformed petroleum naphthas. In the past, it has been the practice in the separation of xylene isomers either to use chemical methods or to distill meta-and para-xylene, ethylbenzene and some paraffins from a fraction containing the xylene isomers, ethylbenzene, and paraffins. Typically, para-xylene and ortho-xylene are produced by recovery of these isomers from a mixed $C_8$ aromatic stream by means of fractionation, adsorption or crystallization. Crystallization is a separation process that takes advantage of the fact that for most xylene mixtures the melting point of para-xylene is higher than the other xylene isomers and crystallizes first. For example, para-xylene crystallizes at 13.3° C., meta-xylene at −47.9° C. and ortho-xylene at −25.2° C.

In a para-xylene crystallizer, the $C_8$ aromatic mixture is cooled using direct or indirect contacting means to the para-xylene crystallization temperature. The effluent from the crystallizer is a slurry comprising para-xylene crystals and mother liquor. The slurry is sent to a separation vessel, for example, a centrifuge, where the mother liquor is separated from the para-xylene crystals. Since the separation of mother liquor and para-xylene crystals is not 100% effective, the para-xylene crystals are generally remelted and recrystallized to achieve higher purity.

The purity of the melted para-xylene recovered from this slurry depends on the amount and composition of the occluded mother liquor accompanying the crystals. Mother liquor is generally present in two forms: (1) mother liquor occlusions within the crystal matrix; and (2) mother liquor that is adhering to surfaces and between crystals. The amount of mother liquor which is within the crystal matrix is dependent on the purity of the mother liquor and the method used to obtain the crystals. The amount of mother liquor which is adhering to the surface of the crystal is dependent on crystal size and shape, mother liquor viscosity and mother liquor purity. Large crystals have the favorable characteristic of containing large spaces between the crystals so that the mother liquor can drain from the crystals more readily. U.S. Pat. No. 2,913,503 describes a process for increasing the para-xylene crystal size using longer crystallization residence time. Other mechanical solutions can also be used to increase the size of the crystal.

Control of the composition of the adhering mother liquor may be accomplished by washing with a foreign substance, for example, propane at its boiling point (U.S. Pat. No. 2,823,241) or aqueous methanol (U.S. Pat. No. 2,724,007); or by washing with a stream containing a high percentage of para-xylene, for example, mother liquor from the second stage (U.S. Pat. Nos. 3,049,575 and 3,197,525).

In a conventional para-xylene crystallization process, the actual crystallization occurs in two parts or sections. The first section is a recovery section for crystallizing the bulk of the para-xylene. The second section is a purification section for enriching the recovered para-xylene. In the recovery section, the para-xylene crystals are generally formed at about −30° C. to −65° C. and are separated from the recovery section mother liquor using a first centrifuge at −65° C. The recovered para-xylene crystals are then remelted, admixed with the recycled purification section mother liquor and passed to the purification section where high purity para-xylene crystals are formed at about 5° C. to −10° C. The purified para-xylene crystals are then separated from the purification section mother liquor. Mother liquor from the recovery section can be sent to a xylene isomerization zone to convert a significant amount of the non-para-xylene isomers to para-xylene which is then recycled back to the recovery section.

The problem with the conventional two-stage para-xylene crystallization process in the recovery section is very energy intensive because the entire mass $C_8$ aromatic feed has to be cooled to the ultimate low temperatures required for effective crystallization of the para-xylene crystals, i.e. −65° C.

U.S. Pat. No. 3,177,265 (issued to Lammers) discloses a process wherein in the recovery section the $C_8$ aromatic is gradually cooled to these low temperatures by staging the recovery section temperatures using two or more crystallizers in series. In the Lammers process, a $C_8$ aromatic hydrocarbon mixture containing 8–25 volume percent para-xylene is combined with recycled purification section mother liquor and fed to the two-stage recovery section. The recovery section comprises two crystallizers and holding tanks having a single set of recovery section centrifuges positioned downstream of the second recovery section crystallizer. In the first crystallizer the $C_8$ aromatic mixture is cooled to −34° C. to −56° C., but no separation of crystals and mother liquor occurs. In the second crystallizer, the effluent from the first crystallizer is cooled to about −65° C. to −76° C. The separation of para-xylene crystals from its mother liquor occurs at this lower temperature. The resulting para-xylene crystals are remelted, admixed with purification section effluent, and passed to the purification section.

U.S. Pat. No. 2,866,833 (issued to Spiller) describes a para-xylene crystallization process that uses a single stage recovery section and a two-stage purification section. In the recovery section, a $C_8$ aromatic mixture containing section. In the recovery section, a $C_8$ aromatic mixture containing about 19 vol. % is chilled to less than −73° C. to form a resulting mixture that is separated into a first solids cake containing 80 wt. % solids and a recovery section mother liquor. Purification of the first solids cake is effected in a purification section that contains two stages for crystallization and separation. In the first stage of the purification section, the first solids cake is melted, mixed in with recycled first purification stage mother liquor and chilled to about −6° C. to −34° C. to form a second solids cake containing about 90-95 wt. % solids and the first purification stage mother liquor. In the second purification stage, first purification stage mother liquor is chilled to about −1° C. to 3° C. to form a third solids cake and a second purification stage mother liquor. The third solids cake is remelted and fed back into the second stage purification stage feed. The second purification stage mother liquor is fed back to the recovery section.

Although the Lammers process may be successful at producing larger para-xylene crystals in the recovery section by staging the temperatures and increasing the residence time in the recovery section of the process, the energy consumption will be high because the entire mass of the $C_8$ aromatic feed has to be cooled to the lowest temperature (−65° C. to −75° C.). Similarly, in the Spiller process, the energy consumption will remain high because the entire mass of the $C_8$ aromatic feed must be cooled to less than −75° C. Further, neither the Lammers nor Spiller process discloses or suggests rejecting the mother liquor to a xylene isomerization unit. Accordingly, a significant portion of the crystallization feed, i.e., the non-para-xylene isomers, is not converted to para-xylene. As a result, the para-xylene yield is substantially less.

There is a need for a crystallization process that: (1) recovers para-xylene crystals using less energy; and (2) increases para-xylene yield from a mixture of $C_8$ aromatic isomers. The objective of the present invention is to address these needs.

SUMMARY OF THE INVENTION

The present invention achieves the objective of recovering para-xylene using less energy by modifying the conventional crystallization recovery section such that para-xylene crystals are first crystallized and separated at a relatively high temperature and then crystallized and separated at a lower temperature. The second objective of increasing para-xylene yield is achieved by rejecting at least a portion of the recovery section mother liquor to a xylene isomerization unit wherein a significant portion of the non-para-xylene isomers are converted to para-xylene under equilibrium conditions.

The present invention is a crystallization process for producing para-xylene crystals from a mixed xylene feedstock which process comprises the steps of: passing at least a portion of the feedstock to a crystallization recovery section comprising: a first stage recovery section which produces first stage recovery section para-xylene crystals and first stage recovery section mother liquor at a first temperature; and a second stage recovery section which produces second stage recovery section para-xylene crystals and second stage recovery section mother liquor at a second temperature which is lower than the first temperature; feeding at least a portion of the first stage recovery section mother liquor to the second stage crystallization recovery section; passing at least a portion of the second stage recovery section mother liquor to a xylene isomerization zone containing an isomerization catalyst at conditions sufficient to produce an isomerate comprising an equilibrium xylene mixture and passing a recycle stream comprising the isomerate to the crystallization recovery section; passing a purification feed stream comprising the first and second stage recovery section para-xylene crystals to a crystallization purification section to produce a purification section effluent stream comprising para-xylene crystals and purification section mother liquor; and separating the purification section effluent stream into purification mother liquor and para-xylene product crystals.

In one embodiment, the present invention is a crystallization process for producing para-xylene crystals from a mixed xylene feedstock which process comprises the steps of: passing at least a portion of the feedstock to a crystallization recovery section comprising: a first stage recovery section which produces first stage recovery section para-xylene crystals and first stage recovery section mother liquor at a temperature of about −35° C. to −50° C.; and a second stage recovery section which produces second stage recovery section para-xylene crystals and second stage recovery section mother liquor at a temperature of about −55° C. to −75° C.; feeding at least a portion of the first stage recovery section mother liquor to the second stage crystallization recovery section; passing at least a portion of the second stage recovery section mother liquor to a xylene isomerization zone containing an isomerization catalyst at conditions sufficient to produce an isomerate comprising an equilibrium xylene mixture and passing a recycle stream comprising the isomerate to the crystallization recovery section; passing a purification feed stream comprising the first and second stage recovery section para-xylene crystals to a crystallization purification section to produce a purification section effluent stream comprising para-xylene crystals and purification section mother liquor; and separating the purification section effluent stream into purification mother liquor and para-xylene product crystals.

In another embodiment, the present invention is a crystallization process for producing para-xylene crystals from a mixed xylene feedstock which process comprises the steps of: passing at least a portion of the feedstock to a crystallization recovery section comprising: a first stage recovery section which produces first stage recovery section para-xylene crystals and first stage recovery section mother liquor at a temperature of about −35° C. to −50° C.; and a second stage recovery section which produces second stage recovery section para-xylene crystals and second stage recovery section mother liquor at a temperature of about −55° C. to −75° C.; feeding at least a portion of the first stage recovery section mother liquor to the second stage crystallization recovery section; passing at least a portion of the second stage recovery section mother liquor to a xylene isomerization zone containing an isomerization catalyst at conditions sufficient to produce an isomerate comprising an equilibrium xylene mixture and passing a recycle stream comprising the isomerate to the crystallization recovery section; passing a purification feed stream comprising the first and second stage recovery section para-xylene crystals to a crystallization purification section to produce a purification section effluent stream comprising para-xylene crystals and purification section mother liquor; separating the purification section effluent stream into purification mother liquor and para-xylene product crystals; and passing at least a portion of the purification section mother liquor to the crystallization recovery section.

DESCRIPTION OF THE DRAWING

The FIGURE is a schematic representation of one embodiment of the present invention.

DESCRIPTION OF THE PREFERRED EMBODIMENT

The $C_8$ aromatic hydrocarbon feedstock of the present invention comprises ortho-, meta-, para-xylene and ethylbenzene. The feedstock may also contain other hydrocarbon classes such as paraffins and naphthenes. Although other hydrocarbon classes may be present in the feedstock of the present invention, it is preferred that the mixture contain no substantial proportion of polymerizable or condensable hydrocarbons. In a preferred embodiment, the source of the $C_8$ aromatic-containing feedstock is a fraction derived from certain petroleum conversion products containing aromatic hydrocarbons and including fractions boiling within the range of about 120° C. to about 145° C. at atmospheric pressure. Suitable fractions utilizable as a feedstock in the present invention may be separated from gasoline produced by subjecting an appropriately boiling petroleum fraction to dehydrogenation as, for example, a hydroformed gasoline boiling range fraction containing naphthenic hydrocarbons. Such gasoline boiling range fractions of petroleum conversion products may be produced either thermally and/or produced in a catalyzed cracking, reforming, or hydroforming unit.

The feedstock of the present invention can be introduced into a separation zone for the removal of $C_9+$ hydrocarbons. In a preferred embodiment, this separation zone is a distillation column generally known as a xylene column. In one embodiment of the present invention, the xylene column is operated at conditions sufficient to separate some or all of the ortho-xylene along with the $C_9+$ hydrocarbons. The ortho-xylene can then be separated as an overhead stream in another distillation column known as an ortho-xylene column. In another embodiment, the xylene column is operated at conditions sufficient to separate some or all of the $C_9+$ hydrocarbons.

The crystallization process of the present invention comprises a recovery section and a purification section. The recovery section comprises a first stage and a second stage. In the first stage, the $C_8$ aromatic feedstock of the present invention is cooled to a temperature of about $-35°$ C. to $-50°$ C., preferably about $-45°$ C. This cooling can be accomplished by internal or external refrigerants. Suitable internal refrigerants include, but are not limited to, ethane, ethylene, liquid $CO_2$, aqueous methanol, ammonia, silicon hydride and brine solution. In one embodiment of the present invention, a solution is added to reduce the crystallization temperature. Suitable temperature reduction solutions include pentane, isopentane, methylhexanes, and m-ethyltoluene.

The crystallizer can be any apparatus known to those skilled in the art for crystallizing para-xylene from a $C_8$ aromatic mixture. In one embodiment of the present invention, the $C_8$ aromatic feedstock is sprayed into a pool of vaporizing refrigerant, the drops falling through the pool, crystals being removed at the bottom, and mother liquor being drawn off at another level. In another embodiment, the crystallizer sparges ethylene into an annular space defined by a cylinder in a tank, the rising and evaporating ethylene produces circulation, and the crystals and mother liquor flow from the top of the annulus to the central part within the cylinder and settle to the bottom. The central zone constitutes a holding zone for the crystal growth. Crystals and mother liquor are withdrawn from the bottom of the unit. In a related embodiment, the refrigerant is sparged into the central cylinder or draft tube, and crystals and mother liquor flow downward through the annular space, as a slow-speed agitator in the conical bottom of the tank prevents consolidation of the crystals.

Scraped-surface chillers can also be used in the crystallization process of the present invention. These chillers are often followed by a holding tank to allow for crystal growth. Suitable operating conditions for these chillers include 5–10 scrapes per minute (RPM × number of blades) and a holding time of at least 30 minutes, preferably about 8 hours in the recovery section. Part of the crystallization feed may be cooled without crystallization in a separate exchanger and mixed with the material from the scraped-surface chiller in the holding tank.

In one embodiment, the crystallizer vessel is an apparatus that combines the functions of the scraped-surface chiller and the holding tank. For example, refrigerant in a jacket surrounding the crystallizer vessel can provide the required cooling while scraper blades keep the build-up of crystals on the internal surface at an acceptable level.

The slurry from the first stage of the recovery section is passed to a first stage centrifuge for separation of the first stage recovery mother liquor from the para-xylene crystals.

After separating the first stage recovery mother liquor from the para-xylene crystals, the para-xylene crystals are remelted and passed to the purification section for enrichment and the mother liquor is passed to the second stage of the recovery section. In the second stage, the first stage mother liquor is cooled to a temperature of about $-55°$ C. to $-75°$ C., preferably about $-65°$ C. In a preferred embodiment, cooling is provided by ethylene vaporization. With the exception of the operating temperature, the operating conditions and apparatus used in the second stage of the recovery section are the same as the operating conditions and apparatus used in the first stage of the recovery section.

In accordance with the present invention, at least a portion of the slurry resulting from the second stage of the recovery section is passed to a second stage centrifuge which separates the para-xylene crystals from the second stage mother liquor.

In accordance with the present invention, at least a portion of the second stage mother liquor is contacted with an isomerization catalyst in an isomerization zone at isomerization conditions sufficient to produce an isomerate comprising an equilibrium xylene mixture.

The isomerization catalyst can be any suitable isomerization catalyst known to those skilled in the art. The catalyst will typically comprise an acidic inorganic oxide support which has incorporated at least one metallic component.

With respect to the inorganic oxide binder utilized in the isomerization catalyst of the present invention, it is preferred that the binder be a porous, adsorptive, high surface area support having a surface area of about 25 $m^2/g$ to about 500 $m^2/g$. The binder should also be uniform in composition and relatively refractory to the conditions utilized in the isomerization process of the present invention. Examples of suitable binders include alumina, silica, silica-alumina, zinc titanium, zirconium, magnesia, thoria, chromia, boria, attapulgus clay, diatomaceous earth, Fuller's earth, kaolin, kieselguhr, and any mixtures thereof. The preferred binder is alumina. Suitable aluminas are the crystalline aluminas known as gamma, beta, and theta. The preferred alumina is gamma-alumina. Preferred binders have an apparent bulk density of about 0.3 g/cc to about 0.8 g/cc and surface area characteristics such that the average pore diameter is about 20 to about 300 Angstroms and the pore volume is about 0.1 cc/g to about 1 cc/g.

With respect to the metallic component of the isomerization catalyst, the preferred metal is a Group VIII metal. Suitable Group VIII metals include platinum, palladium, rhodium, ruthenium, osmium, and iridium, preferably platinum. The Group VIII metal may exist within the final catalyst as an oxide, sulfide, halide, oxysulfide, or as an elemental metal, or as any combination thereof. The Group VIII metal component generally comprises about 0.01 wt. % to about 2 wt. % of the final component, preferably 0.05 to 1.0 wt. %.

The Group VIII metal component may be incorporated into the isomerization catalyst of the present invention using any suitable means which results in the metal distribution disclosed herein. Suitable examples are ion exchange and impregnation. The preferred method of preparing the catalyst normally involves the use of a water-soluble decomposable compound of a Group VIII metal to impregnate a calcined zeolite/binder composite. For example, the Group VIII metal may be added to a calcined hydrogel by commingling the calcined composite with an aqueous solution of chloroplatinic or chloropalladic acid.

In a preferred embodiment, the isomerization catalyst of the present invention contains a lead component. The lead component may be incorporated into the catalytic composite in any suitable manner to effectively disperse this component on the individual moieties of the composite and to achieve the disclosed distribution of lead between the zeolite moiety and the binder moiety. A suitable method can include coprecipitation or congelation with the inorganic oxide binder, ion-exchange with the inorganic oxide binder, or impregnation of the catalyst at any stage of precipitation. One preferred method of incorporating the lead component into the catalytic composite involves the addition of suitable soluble lead compounds such as lead nitrate, lead acetate, lead citrate, lead formate, and the like to the zeolite-containing hydrosol of the inorganic oxide, and then combining the hydrosol with a suitable gelling agent and dispersing the resulting mixture into an oil bath. After calcining the gelled hydrosol, there is obtained a binder material having a uniform dispersion of lead oxide in intimate combination principally with the inorganic oxide binder.

Another preferred method of incorporating the lead component into the isomerization catalyst composite involves the use of a soluble, decomposable compound of lead to impregnate and uniformly disperse the lead on the composite. In general, the lead component can be impregnated prior to, simultaneously with, or after the Group VIII metal is added to the carrier.

In another embodiment, the isomerization catalyst of the present

In another embodiment, the isomerization catalyst of the present invention contains a halogen component. The halogen is combined with the carrier material or with the other ingredients of the catalyst in the form of the corresponding halide. Suitable halogens include chlorine, iodine, bromine, or any mixtures thereof, preferably fluorine and chlorine. The halogen may be added to the carrier material in any suitable manner known to those skilled in the art either during preparation of the carrier material or before or after the addition of the other components.

Regardless of how the isomerization catalyst components are combined with the porous carrier material, the catalyst composite is dried at a temperature of from about 100° C. to about 320° C. for a period of about 2 to 24 hours. The desired composite is then calcined at a temperature of about 400° C. to about 600° C. in air at atmospheric conditions for a period of about 0.1 to 10 hours to convert the metallic compounds substantially to the oxide form. The resultant calcined composite may be subjected to a substantially water-free reduction step prior to its use in the conversion of hydrocarbons. The reducing agent, which is preferably hydrogen, contacts the catalyst at conditions including a temperature of about 200° C. to about 650° C. for a period of about 0.5 to 10 hours to reduce substantially all of the Group VIII metal components to the metallic state.

In a preferred embodiment, the isomerization catalyst of the present invention comprises a Group VIII metal, a lead component sufficient to amount to an atomic ratio of lead to a Group VIII metal from about 2:1 to about 10:1, from about 1 to 20 wt. % of a pentasil zeolite, and an inorganic binder, wherein from about 80 to 100 wt. % of the Group VIII metal and about 60 to 100 wt. % of the lead component are contained in the inorganic binder.

The isomerization catalyst of the present invention is disposed in an isomerization zone. The catalyst can be arranged in a fixed-bed system, a moving-bed system, a fluidized bed system, or in a batch-type operation. In view of the danger of catalyst attrition loss and of operational advantages, it is preferred to use a fixed-bed system. In this system, a hydrogen gas and the feedstock are preheated by suitable heating means to the desired reaction temperature and then passed into an isomerization zone containing a fixed bed of catalyst. The isomerization conversion zone may be one or more separate reactors with suitable means therebetween to ensure that the desired isomerization temperature is maintained at the entrance to each zone. The reactants may be contacted with the catalyst in upward, downward, or radial flow fashion. Further, the reactants may be in liquid phase, vapor phase, or vapor/liquid phase when contacting the catalyst.

Suitable isomerization conditions include a temperature of about 0° C. to about 600° C., preferably 350° C. to 500° C., a pressure of about 1 to 100 atmospheres, preferably 2 to 30 atmospheres, a hydrogen to hydrocarbon mole ratio of about 0.5:1 to about 15:1, and a liquid hourly space velocity of about 0.5 to 30 $hr^{-1}$.

The para-xylene which is crystallized and separated in the first and second stages of the recovery section of the crystallization process is remelted, admixed with recycled purification section mother liquor and fed to the purification section. In the purification section, the feed slurry is cooled to about 0° C. to −10° C. In a preferred embodiment, cooling is provided by propane vaporization. Other than the temperature, the operating conditions and crystallizer apparatus used in the purification section can be the same as that used for the recovery stage.

The slurry exiting the purification section is passed to a purification centrifuge which separates the para-xylene product crystals from the purification stage mother liquor. At least a portion of the purification mother liquor is recycled to the recovery section. The remainder of the purification mother liquor is recycled to the purification feed and admixed with melted para-xylene crystals recovered from the recovery section.

Additional treatment of the purification para-xylene crystals can include washing the para-xylene crystals with a variety of compounds including but not limited to para-xylene product, normal pentane, toluene, aqueous alcohols and aqueous salts to improve final product purity by removing adhering second stage mother liquor. After melting the crystals, it may be necessary to feed the resulting mixture to a fractionation column to separate the para-xylene product from the wash liquor.

Referring to the figure, mixed xylene feedstock 1 is admixed with recycle isomerate 50 to form combined feed 2. Xylene column 4 receives combined feed 2 and separates $C_9$ aromatics into bottoms stream 8. A mixture of $C_8$ aromatics exits in overhead stream 6. Overhead stream 6 is admixed with purification section mother liquor via stream 10 and combined feed 12 is fed to first stage 14 of recovery section 5 (as indicated by the dotted box). In first stage 14, combined feed is cooled to a temperature of about −45° C. A slurry containing para-xylene crystals and first stage recovery mother liquor exits first stage 14 in stream 16. This slurry is fed to first stage recovery centrifuge 18 which separates the slurry into para-xylene crystals (stream 22) and first stage recovery mother liquor (stream 20).

The first stage recovery mother liquor is fed to second stage 24 of recovery section 5 via line 20. In second stage 24, mother liquor is cooled to a temperature of about −65° C. A slurry containing para-xylene crystals and second stage recovery mother liquor exits the second stage in stream 26. This slurry is fed to second stage recovery centrifuge 28 which separates the slurry into para-xylene crystals (stream 30) and second stage recovery mother liquor (stream 32).

The second stage recovery mother liquor is fed to xylene isomerization section 46 through stream 32. In xylene isomerization section 46, second stage recovery mother liquor is contacted under isomerization conditions in the presence of an isomerization catalyst to re-establish an equilibrium xylene mixture which exits isomerization section 46 by line 50. This xylene isomerization isomerate is admixed with the mixed xylene feedstock (stream 1) and recycled to xylene column 4. Some isomerization losses due to for example ring loss will occur. This loss is represented in the figure by stream 48.

The crystalline para-xylene recovered in recovery stage 5 through lines 22 and 30 is remelted, combined with purification mother liquor from stream 44 and fed to purification section 36 via line 34. In purification section 36, the combined feed is cooled to a temperature of about 0° C. to −10° C. to produce a slurry containing para-xylene product crystals and purification section mother liquor. This slurry exits purification section 36 via line 38 and is passed to purification centrifuge 40 which separates the slurry into para-xylene product crystals by line 42 and purification mother liquor through line 44. At least a portion of the purification stage mother liquor is recycled back to first stage 14 of recovery section 5. The remaining purification mother liquor is recycled to the feed of purification section 36 and admixed with remelted para-xylene crystals recovered in recovery section 5.

EXAMPLES

Introduction

The following examples will show that the present invention has clear advantages over the conventional single stage recovery section and single stage purification section with respect to the refrigeration duty required to recover the para-xylene from feed and recycle streams. Although not wanting to be limited to a particular theory, it is believed that the advantage the present invention has in refrigeration duty is attributable to separating para-xylene crystals from the mother liquor at an intermediate temperature (rather than the ultimate low temperature) and thereby avoiding having to cool these crystals down to the lowest temperature.

The following examples will illustrate the results of heat balance calculations carried out on both the present invention and the conventional two-stage crystallization process. The two flow schemes were simulated using computer models. Every effort was made to maintain common operating conditions to ensure the comparison was on a fair basis. The xylene feed mixture composition for each case was the following: 17.4 wt. % ethylbenzene, 18.2 wt. % para-xylene, 39.5 wt. % meta-xylene, 24.0 wt. % ortho-xylene and 0.9 wt. % $C_9$+hydrocarbons. These examples assume no ortho-xylene co-production.

In the crystallization portion of the process, the following assumptions were made: (1) the first stage recovery is set by eutectic limit of approximately 9% para-xylene in the mother liquor (the governing eutectic was para-xylene/meta-xylene); (2) percent solids exiting the first stage of about 15 wt. % to about 25 wt. %, with separated mother liquor being recycled to the isomerization unit. The mother liquor hold-up on the para-xylene crystals exiting the first stage separation either by occlusion or by surface adhesion is 10%. The purity of the para-xylene crystals exiting the first stage was assumed to be 92%.

The second stage recovery was set by a maximum solids content of 40% exiting the crystallizer. Second mother liquor is recycled to the second stage inlet to dilute the feed to 80% para-xylene, the remaining second mother liquor being recycled to the first stage inlet. The final washing of the second stage para-xylene product crystals is performed to achieve a product purity of 99.75%.

In the isomerization section, the xylene distribution is 23.7% para-xylene, 55.3% meta-xylene and 21.0% ortho-xylene. The xylene ring loss is 2.2%. Xylene ring loss to A9 crystallizer is 40%. The ethylbenzene conversion is 65%.

EXAMPLE 1

In Example 1, a $C_8$ aromatic feed mixture having the composition described above is fed to a single stage recovery section at a rate of about 66,191 Kg/hr. In the recovery section crystallizer, the $C_8$ aromatic stream is cooled to a temperature of about −65° C. using a direct contact refrigerant (ethylene). The slurry exiting the recovery section crystallizer is passed to a recovery section centrifuge which separates the para-xylene crystals (including some occluded mother liquor) and mother liquor. The mother liquor is passed to a xylene isomerization unit at a rate of about 57,313 Kg/hr. The xylene isomerization unit converts non-para-xylene components such as meta- and ortho-xylene to para-xylene under equilibrium conditions.

Para-xylene crystals are remelted, admixed with purification section mother liquor and fed to a purification section crystallizer at a rate of about 23,204 Kg/hr. The purification section crystallizer is maintained at a temperature of about −10° C. and is cooled by propane evaporation. The slurry exiting the purification section crystallizer is passed to a purification section centrifuge and is separated into para-xylene product crystals and purification section mother liquor. Approximately 9276 Kg/hr. of para-xylene crystal product is produced. The purification section mother liquor is recycled to the purification section feed and admixed with the remelted crystals from the recovery stage.

The refrigeration duty of the recovery section for the conventional process is 125,010 kilocalories per metric ton of product.

EXAMPLE 2

In Example 2, a $C_8$ aromatic feed mixture having the same composition as the feed in Example 1 is fed to a two-stage recovery section (containing a first stage recovery crystallizer and a second stage recovery crystallizer) at a rate of about 66,364 Kg/hr. In the first stage recovery crystallizer, the $C_8$ aromatic stream is cooled to a temperature of about −45° C. using a direct contact refrigerant (ethylene). The slurry exiting the first stage recovery crystallizer is passed to a first stage recovery section centrifuge which separates the slurry into first stage para-xylene crystals (including some occluded mother liquor) and first stage mother liquor.

The first stage mother liquor is passed to a second stage recovery crystallizer and cooled to a temperature of about −65° C. Ethylene is used as a cooling means. The slurry exiting the second stage crystallizer is passed to a second stage centrifuge which separates the slurry into second stage para-xylene crystals and second stage mother liquor. The second stage mother liquor is passed to a xylene isomerization unit at a rate of about 57,493 Kg/hr. The isomerization unit converts non-para-xylene components to para-xylene under equilibrium conditions with the other xylene isomers.

First and second stage crystals exit the recovery section and are remelted, admixed with purification section mother liquor and fed to the purification section crystallizer at rate of 23,182 Kg/hr. The purification section crystallizer is maintained at a temperature of about −10° C. and is cooled by propane evaporation. The slurry exiting the purification section crystallizer is passed to a purification section centrifuge and is separated into para-xylene product crystals and purification section mother liquor. Product para-xylene crystals are produced at a rate of 9274 Kg/hr. The purification mother liquor is recycled to the purification feed and admixed with the remelted crystals from the recovery stage.

The refrigeration duty of the recovery section for the present invention is 115,400 kilocalories per metric ton of product. This is a 7.7% reduction over the conventional process modeled in Example 1.

What is claimed is:

1. A crystallization process for producing para-xylene crystals from a mixed xylene feedstock which process comprises the steps of:
   (a) passing at least a portion of said feedstock to a crystallization recovery section comprising:
      (i) a first stage recovery section which produces first stage recovery section para-xylene crystals and first stage recovery section mother liquor at a first temperature; and
      (ii) a second stage recovery section which produces second stage recovery section para-xylene crystals and second stage recovery section mother liquor temperature which is lower than said first temperature;
   (b) feeding at least a portion of said first stage recovery section mother liquor to said second stage crystallization recovery section;
   (c) passing at least a portion of said second stage recovery section mother liquor to a xylene isomerization zone containing an isomerization catalyst at conditions sufficient to produce an isomerate comprising an equilibrium xylene mixture and passing a recycle stream comprising said isomerate to said crystallization recovery section;
   (d) passing a purification feed stream comprising said first and second stage recovery section para-xylene crystals to a crystallization purification section to produce a purification section effluent stream comprising para-xylene crystals and purification section mother liquor; and
   (e) separating said purification section effluent stream into purification mother liquor and para-xylene product crystals.

2. The process of claim 1 wherein said first temperature is about −35° C. to −50° C.

3. The process of claim 1 wherein said second temperature is about −55° C. to −75° C.

4. The process of claim 1 wherein at least a portion of said purification section mother liquor is recycled to said crystallization recovery section.

5. The process of claim 1 wherein at least a portion of said purification section mother liquor is commingled with said admixture from step (d) and recycled to said crystallization purification section.

6. The process of claim 1 wherein said xylene feedstock is passed to a xylene column to produce a xylene column effluent stream comprising $C_9+$ hydrocarbons prior to introducing said feedstock to said crystallization recovery section.

7. The process of claim 6 further comprising operating said xylene column at conditions sufficient to produce a xylene column effluent stream which comprises $C_9+$ hydrocarbons and ortho-xylene.

8. The process of claim 7 further comprising passing said xylene column effluent stream to a ortho-xylene column to produce an ortho-xylene product stream.

9. A crystallization process for producing para-xylene crystals from a mixed xylene feedstock which process comprises the steps of:
   (a) passing at least a portion of said feedstock to a crystallization recovery section comprising:
      (i) a first stage recovery section which produces first stage recovery section para-xylene crystals and first stage recovery section mother liquor at a temperature of about −35° C. to −50° C.; and
      (ii) a second stage recovery section which produces second stage recovery section para-xylene crystals and second stage recovery section mother liquor at a temperature of about −55° C. to −75° C.;
   (b) feeding at least a portion of said first stage recovery section mother liquor to said second stage crystallization recovery section;

(c) passing at least a portion of said second stage recovery section mother liquor to a xylene isomerization zone containing an isomerization catalyst at conditions sufficient to produce an isomerate comprising an equilibrium xylene mixture and passing a recycle stream comprising said isomerate to said crystallization recovery section;

(d) passing a purification feed stream comprising said first and second stage recovery section para-xylene crystals to a crystallization purification section to produce a purification section effluent stream comprising para-xylene crystals and purification section mother liquor; and (e) separating said purification section effluent stream into purification mother liquor and para-xylene product crystals.

10. The process of claim 9 wherein at least a portion of said purification section mother liquor is recycled to said crystallization purification section.

11. The process of claim 9 wherein said xylene feedstock is passed to a xylene column to produce a xylene column effluent stream comprising $C_9+$ hydrocarbons prior to introducing said feedstock to said crystallization recovery section.

12. The process of claim 9 further comprising operating said xylene column at conditions sufficient to produce a xylene column effluent stream which comprises $C_9+$ hydrocarbons and ortho-xylene.

13. The process of claim 12 further comprising passing said xylene column effluent stream to an ortho-xylene column to produce an ortho-xylene product stream.

14. A crystallization process for producing para-xylene crystals from a mixed xylene feedstock which process comprises the steps of:

(a) passing at least a portion of said feedstock to a crystallization recovery section comprising:

(i) a first stage recovery section which produces first stage recovery section para-xylene crystals and first stage recovery section mother liquor at a temperature of about $-35°$ C. to $-50°$ C.; and (ii) a second stage recovery section which produces second stage recovery section para-xylene crystals and second stage recovery section mother liquor at a temperature of about $-55°$ C. to $-75°$ C.;

(b) feeding at least a portion of said first stage recovery section mother liquor to said second stage crystallization recovery section;

(c) passing at least a portion of said second stage recovery section mother liquor to a xylene isomerization zone containing an isomerization catalyst at conditions sufficient to produce an isomerate comprising an equilibrium xylene mixture and passing a recycle stream comprising said isomerate to said crystallization recovery section;

(d) passing a purification feed stream comprising said first and second stage recovery section para-xylene crystals to a crystallization purification section to produce a purification section effluent stream comprising para-xylene crystals and purification section mother liquor;

(e) separating said purification section effluent stream into purification mother liquor and para-xylene product crystals; and (f) passing at least a portion of said purification section mother liquor to said crystallization recovery section.

15. The process of claim 14 wherein said xylene feedstock is passed to a xylene column to produce a xylene column effluent stream comprising $C_9+$ hydrocarbons prior to introducing said feedstock to said crystallization recovery section.

16. The process of claim 14 further comprising operating said xylene column at conditions sufficient to produce a xylene column effluent stream which comprises $C_9+$ hydrocarbons and ortho-xylene.

17. The process of claim 16 further comprising passing said xylene column effluent stream to an ortho-xylene column to produce an ortho-xylene product stream.

* * * * *